(12) United States Patent
Thothathri

(10) Patent No.: US 7,585,898 B2
(45) Date of Patent: Sep. 8, 2009

(54) COMPOSITION FOR GROWTH OF DIATOM ALGAE

(76) Inventor: Sampath Kumar Thothathri, 651, 11th Main Road, 5th Block, Jayanagar, Bangalore 560 041, Karnataka (IN)

( * ) Notice: Subject to any disclaimer, the term of this patent is extended or adjusted under 35 U.S.C. 154(b) by 244 days.

(21) Appl. No.: 11/596,406

(22) PCT Filed: Jun. 7, 2005

(86) PCT No.: PCT/IN2005/000195

§ 371 (c)(1),
(2), (4) Date: Nov. 14, 2006

(87) PCT Pub. No.: WO2005/121313

PCT Pub. Date: Dec. 22, 2005

(65) Prior Publication Data

US 2007/0275856 A1    Nov. 29, 2007

(30) Foreign Application Priority Data

Jun. 7, 2004    (IN) .......................... 525/CHE/2004

(51) Int. Cl.
  *C01B 33/113*    (2006.01)
  *A01G 7/00*    (2006.01)
  *C12N 1/12*    (2006.01)
  *C01B 33/20*    (2006.01)
  *A01H 13/00*    (2006.01)

(52) U.S. Cl. .......................... 516/80; 47/1.5; 435/257.1; 435/257.2; 435/257.3; 435/257.4; 435/257.5; 435/257.6

(58) Field of Classification Search ................ 504/152, 504/282, 246; 548/357.2, 544, 359.1; 516/80, 516/77
See application file for complete search history.

(56) References Cited

U.S. PATENT DOCUMENTS

| 4,563,298 | A | * | 1/1986 | Keiser ........................ 516/80 |
| 6,458,179 | B1 | | 10/2002 | Puskarich |
| 6,555,228 | B2 | | 4/2003 | Guritza |
| 6,918,954 | B2 | * | 7/2005 | Perander et al. .......... 106/18.12 |
| 2003/0089668 | A1 | | 5/2003 | Moffett |

* cited by examiner

*Primary Examiner*—Johann R Richter
*Assistant Examiner*—Danielle Sullivan
(74) *Attorney, Agent, or Firm*—Foley & Lardner LLP

(57) ABSTRACT

The present invention relates to a composition for a copious bloom of diatom algae comprising macro and or micro nutrients adsorbed on metalate modified silica sol. The present invention further relates to a process for preparing an aqueous dispersion of a composition comprising of iron adsorbed onto metalate modified silica sol containing 0.01% to 50% of Fe, and a micronutrient adsorbed onto metalate modified silica sol consisting of Mn, Zn, Co, Cu, Mo, B, V, Ni, Se, I, Fl, Cr, Cd and mixtures thereof in the proportion 0.001% to 30% of the weight of silica and macronutrient adsorbed onto metalate modified silica sol consisting of N, P, K, Mg, Ca, S, Cl, Na the elements of each macronutrient varying from 1% to 50% of the silica.

16 Claims, No Drawings

COMPOSITION FOR GROWTH OF DIATOM ALGAE

FIELD OF INVENTION

The present invention relates to increase the production of diatom algae either in water or on the soil. The invention is aimed to a predominant production of diatom algae thus achieving several objectives such as enhancement of oil (fossil fuel) production, cleansing of water pollution, reduction of Green House Effect by faster consumption of carbon di-oxide required for photosynthesis by growing algae and few other processes as described herein. More particularly the present invention relates to silica nutrient, macro and micronutrient for growth of diatom algae.

DESCRIPTION OF THE RELATED ART

The Men have been trying from long time to duplicate nature's creations and processes and have been quite successful resulting in very large benefits. Algae are the basis of the food chain in the marine world. Diatom algae having silica walls are the most prolific growth and food creators that are responsible for the productivity of the oceans. As compared to other green algae and blue green algae having cellulose cell walls that are not easily digestible, diatoms having silica cell wall is easily absorbed and digested by the starting members of the food chain like zooplankton and fish etc. Analysis and speculation indicate that silica is in the form of monomeric orthosilicic acid $Si(OH)_4$ formed by the depolymerization of solid or colloidal silica. Many textbooks have written volumes on the role of silica, their form and solubility etc on the diatom growth.

The deficiency of the silica in the form acceptable for the biological growth of diatoms is the limiting factor in the seas. Sometimes analysis of the seawater indicates that it contains silica but there is no diatom bloom. Another hypothesis was that the sea was lacking in iron and hence algae were not blooming. The SOFEX project was undertaken to test John martin's Iron hypothesis. However the results were indifferent.

The burning of fossil fuels resulting in release of carbon dioxide into the atmosphere has enhanced the greenhouse effect leading to global warming. The nations want the extra carbon dioxide to be absorbed by the oceans and converted to food. The productivity of the oceans has been poor due to lack of plankton growth. Adding the appropriate nutrients can fuel diatom growth and then most of the excess carbon dioxide can be absorbed by the growing algae due to photosynthesis and release of oxygen with the manufacture of food. In addition to this the oceans and lakes have been polluted with excess nitrate and phosphate from land run offs and untreated wastes and sewage that toxic species of phytoplankton have started proliferating resulting in problems for the people at large. Examples of "RED TIDES" are well known. The excess nitrate, phosphate, and sewage have to be converted to food.

It is very well known that nutrients like nitrogen, phosphorous, other macro, micro nutrients and vitamins are required for the growth of all algae. Although iron is the biggest micronutrient required for algal growth there are other very important micronutrients that are required in extremely small quantities but are not readily available in the seawater especially in the alkaline salty conditions. Examples are Manganese, zinc, cobalt and copper. All these micronutrients have to be made available in extremely small quantities for growth of algae. Diatom algae are special in which a silica nutrient is required over and above the other nutrient since the cell walls have silica from 4% to 20% of the dry weight of the cell.

Reference for reading: The physiological ecology of phytoplankton "studies in ecology" Vol. 7 by I. MORRIS.

What is known of prior art is pretty rudimentary written in textbooks. The addition of silicates with other nutrients coupled with chelating agents like EDTA etc. are known to bring a bloom of diatom algae. The following are some of the U.S. patents that have mentioned about producing diatoms.

U.S. Pat. Nos. 5,567,732, 5,244,921 Kyle, et all Eicosapentaenoic acid-containing oil and methods of its production.

In this patent, diatoms are grown using Sodium metasilicate in growth medium composition.

U.S. Pat. No. 6,199,317 Saiki et all—Materials for growing algae and artificial fishing banks.

In this diatoms are grown using ferrous ions released into water.

U.S. Pat. No. 5,965,117 Howard et all Water buoyant particulate material containing micronutrients for phytoplankton.

U.S. patent application 20040093785 Markels, Michael J R Method of increasing fish catch in the ocean May 20, 2004.

Apart from the use of organic compounds for chelating the elements, a method for making the elements available in a particulate form by which it is biologically available in the growth media is just not described in any prior art.

The inorganic silicates used to provide source of silica is by and large useless since they are not absorbed and precipitate out of solution. If you require a sustained and widespread diatom bloom the silica nutrient should be in the solution in an acceptable form for growth and absorption. The earlier U.S. Pat. Nos. 5,567,732 and 5,244,921 claiming use of sodium metasilicate for diatom bloom is too elementary and not sustainable for large-scale diatom production. U.S. Pat. No. 6,199,317 using ferrous ions may be of help if water contains soluble silica. There is this iron hypothesis theory by J. H. Martin mentioned in "Testing the iron hypothesis in eco systems of the equatorial pacific ocean" Nature Vol: 371, Sep. 8, 1998 pp 123-129. The success, if any is very limited and does not prove or disprove the theory. If silicic acid or silica sol is used, they will polymerize under the conditions and precipitate out as silica and hence will no longer be available as nutrient. Further there is some truth that iron is required for algal growth but inorganic iron salts precipitates out under seawater conditions and hence cannot help. If soluble salts of the various elements are added to the water some of them react with each other and become biologically unavailable. The oxidising atmosphere in the water converts most elements into their oxides making it sparingly soluble. The interaction of conflicting anions and cations results in some of the elements going out of solution. For ex. soluble calcium salts react with phosphate and precipitate out.

None in the prior art have conceived of a comprehensive method of delivering the silica nutrient that will deliver silica with the micronutrient required to the diatoms in the form that the diatoms can absorb, assimilate and grow. In cases where the macro nutrients are deficient the method of delivery is not mentioned by any one.

Although the alumina modified silica sol has been known since 1959, it has not been used as source for silica nutrient since by itself it cannot favor the growth of diatoms in the absence of soluble iron and other deficient macro and micro nutrients in the system. Seawater being alkaline in nature and having dissolved salts of sodium, potassium, calcium etc. the solubility of iron, zinc, manganese copper etc. is negligible, and the solubility and presence of silica as a monomer is very much reduced. In this invention the iron and other micronutrients is adsorbed onto the alumina modified silica sol with the result that the iron and other micronutrients cannot precipitate out from the sea water even though the water is alkaline and dissolved salts are present. Iron plays a crucial role in the bioenergetics of carbon and nitrogen metabolism and is required for the synthesis of chlorophyll and reduction of nitrate. Cobalt is required for synthesis of vitamin B12 and manganese is essential for enzyme activation. When practical tests were done in backwaters, a copious bloom of diatoms was obtained on dosing this iron and micronutrient complexed alumina modified silica sol.

The prior art does not describe any product as a silica nutrient that can bring about copious diatom bloom in seawater conditions. The prior art is only suggestive of silicates and other chemicals. This invention provides a product that can directly supply the silica nutrient in conjunction with the required micronutrient for the bloom of diatoms. This invention also identifies the nature and form of the compound that is absorbed for providing the diatom bloom. Use of other chelated nutrients as mentioned in invention US patent application no. 20040093785 by Markels assume that silica is available in the water in the form that can be absorbed and only chelated nutrients are lacking. Further no claim has been made for the exact chelating compound. In the other patents, using inorganic silicates will not remain in solution and sustained diatom bloom is not possible. This invention gives a comprehensive solution to the problem of creating a diatom bloom.

All organic compounds of the nutrient elements have to undergo mineralization of nutrients before they become available to the growing algae. In this invention all the nutrients are in an inorganic mineral form adsorbed onto silica in the form of very fine particles ranging from less than 1 mill micron to 150 mill micron. The smaller the particle the more surface area it has and has a higher capacity to adsorb micro and macro elements. The particle size also has a bearing on the size of the diatoms that can use it as a source of nutrients. The Silica becomes both the carrier for other nutrients and the nutrient by itself, like a cone ice-cream where both the ice-cream and the cone are eaten.

Once all the nutrients are available in the water in the form that can be absorbed by the diatom algae, the bloom of diatoms is very fast. As the diatoms bloom it takes away all the surplus nutrients in the water medium with the result that other plants, algal species etc. are denied their nutrients, hence they slowly die out of the medium. The diatom algae, based on the nitrogen available, produces protein and oil that is consumed by zooplankton and in turn it becomes food for fishes and marine animals. When the diatoms undergo stress due to lack of Nitrogen and in reducing conditions they turn to production of more oil and less protein. It is believed that the world's petroleum resources have, been the result of the diatoms blooming and producing oil.

SUMMARY OF THE PRESENT INVENTION

Therefore the object of the invention is to provide a composition either in sol form or in redispersable dried particulate form, for a copious bloom of diatom algae comprising macro and/or micro nutrients adsorbed on metalate modified silica sol.

The other object of the invention is to provide a composition wherein the quantity of micro and macro nutrients to be adsorbed on a metalate modified silica sol preferably on alumina modified silica sol varies with the requirement such as type of water to be treated, conditions of the soil such as pH and on the other floura needed to be eliminated from the surroundings thus enabling the predominant growth of diatom algae at a faster rate.

The other object is use of composition of the present invention for the copious bloom of diatom algae wherein the biological conditions for photosynthesis include sunlight or other sources of light for photosynthesis, removal of toxic metals and compounds which inhibit growth of algae, provision of starter culture either naturally or added externally.

It is another object of the present invention to provide a process for preparing an aqueous dispersion of a composition comprising of iron adsorbed onto metalate modified silica sol containing 0.1% to 50% of Fe, and a micronutrient adsorbed onto metalate modified silica sol consisting of Mn, Zn, Co, Cu, Mo, B, V, Ni, Se, I, Fl, Cr, Cd and mixtures thereof in the proportion 0.001% to 30% of the silica surface, and macronutrient adsorbed onto metalate modified silica sol consisting of N, P, K, Mg, Ca, S, Cl, Na the elements of each macronutrient varying from 1% to 50% of the silica.

It is another object of the invention to provide a process for stimulating photosynthetic phytoplankton growth in ocean, lake, river or a body of water, devoid of, or deficient in, such growth, said process comprising adding of a product composition of the present invention to the said ocean, lake, river or a body of water.

It is another object of the present invention to provide a process for the reduction of global carbon dioxide by stimulated generation of oceanic photosynthetic phytoplankton using the product composition of the present invention.

It is another object of the invention to provide a process to increase marine or fresh water food by the stimulated generation of photosynthetic phytoplankton using the product composition of the present invention.

It is another object of the invention to provide a process to remove the excess nutrients of N and P from the body of water and by photosynthesis produces oxygen thereby reclaiming and bringing to life water bodies polluted by sewage and other pollutants and those in a state of eutrophication.

Another object of the present invention is to provide a process by which toxic and waste algal species growth is reduced and replaced with growth of useful phytoplankton, the prevention and removal of wild water plants, water weeds, water hyacinth, in any body of water by using the product composition of the present invention.

Another object of the present invention is to provide a process by which sewage, polluted, and effluent water is treated to reduce the Odour, BOD, COD, colour and if necessary convert the nutrient load to marine or fresh water food by using the product composition of the present invention.

In one of the embodiments of the present invention there is to provide a composition wherein the Iron is preferentially adsorbed from 0.01% to 50% of the weight of the silica before the adsorption of other micro and macro nutrients.

Another object of the invention is to treat the sea water or fresh water or polluted water or sewage water or effluent water or a combination thereof by using the composition of the present invention.

In one of the embodiments of the present invention wherein micro and macro nutrients are adsorbed on the metalate modified silica preferably using their corresponding salts.

In one of the embodiments of the present invention wherein the composition is in the form of an aqueous sol, or wet to dry redispersible sol particles, comprising of an iron adsorbed onto metalate modified silica sol having iron in adsorbed form with metalate modified silica sol, with elemental iron varying from 0.01% to 50% of the weight of silica, used alone or in conjunction with other micronutrients and macronutrients adsorbed onto metalate modified silica sol, with each elemental micronutrient varying in concentration from 0.001% to 30% of the weight of silica, and each elemental macronutrient varying in concentration from 1% to 50% of the weight of silica after ensuring the availability of other necessary balancing macronutrients, micronutrients, vitamins, biological conditions for photosynthesis, available either naturally in the growth system or by external addition, for the growth of phytoplankton especially DIATOM ALGAE in seawater, fresh water, polluted water, sewage waters, effluent waters and mixtures thereof and for growth of plants in land and water that can use the micro and macronutrients in a soluble form under varying soil pH conditions.

The source of iron is selected from the group consisting of elemental iron, ferrous sulphate, ferrous ammonium sulphate, ferrous chloride, ferric chloride, ferric nitrate, oxides of iron, mixed metal oxides comprising iron, hydroxides of iron, iron sub oxides, oxyhalides, mixtures thereof, inorganic compounds of iron, organic forms of iron and chelated iron. Vitamins are also adsorbed similar way as other micro macro nutrients are adsorbed. The most preferred vitamins are selected from the group of B complex.

DETAILED DESCRIPTION OF THE INVENTION

This invention relates to development of a Silica nutrient delivered with the macro and micronutrient required for the growth of diatom algae. The base material for nutrient silica is modified silica sol based on U.S. Pat. No. 2,892,797 by Guy. B. Alexander and Ralph K.ller patented on $30^{th}$ Jun. 1959. The details of the preparation of the modified silica sol are mentioned in the patent. Alumina modified silica sol is the preferred one. The particle size of the sol may vary from 5 to 150 mill microns. It is preferable to have between 5 and 30 mill microns. In a typical example a silica sol of 15 nm particles modified in this way with sodium aluminate, the incorporation of only 0.66% by weight of $Al_2O_3$ based on silica was sufficient to give stability for the sol in seawater conditions. Alumina modified silica sol based on U.S. Pat. No. 2,892,797 is miscible with seawater in all proportions without gelling or precipitation unlike unmodified silica sol. The alumina modified silica sol is available as a commercial product called LUDOX AM from Du Pont. However this compound by itself is not enough to grow diatoms in the seawater in the absence of iron and other micro and macro nutrients in the seawater.

By the process of this invention alumina modified silica sol made as per U.S. Pat. No. 2,892,797 is treated with a limited quantity of a solution of an iron salt such that the iron is adsorbed on the silica sol indicated by the discharge of the colour. The iron salt is absorbed on to the surface of the silica forming a physical bond. Similarly very small quantities of other micronutrients like Manganese, zinc, cobalt, copper, Molybdenum nickel, Vanadium, Boron, Selenium, chromium, Iodine, Fluorine, cadmium etc. in a soluble form can be adsorbed on to a alumina modified silica sol. In the same way, macronutrients like phosphorous, potassium, nitrate, calcium, magnesium, chloride, sulphur in the form of a salt solution can be adsorbed onto an alumina modified silica sol and used. A mixture of iron adsorbed alumina modified silica sol and the other micronutrient and macronutrient adsorbed onto alumina modified silica sol is made. This solution can be directly used as a source of silica and micronutrient for growing diatoms in the seawater/fresh water/polluted/sewage waters or can be dried to powder, that is redispersible in seawater/fresh water and used as a source of silica nutrient and micronutrients.

Those macronutrients and micronutrients that is naturally soluble in fresh and seawater without precipitation can be added to the water directly. Only those that precipitate out and those that react with other anion and cations resulting in an insoluble precipitate need to be adsorbed onto the silica surface to avoid interaction and precipitation.

This iron and other micro and macro nutrient absorbed on alumina modified silica sol is miscible with seawater in all proportions without gelling or precipitation and forms the active silica nutrient that will enable diatoms to grow in large quantities. All Micro and Macro nutrients can be absorbed onto alumina modified silica sol using the required soluble salt solution. The preferred iron salt is ferric chloride but other iron salts can be used. The preferred salt for other micronutrients is in the chloride form.

Algae require the iron as a micronutrient and hence very small quantity in the region of micrograms is necessary. However if the deficiency in the growth medium is mainly iron then more quantity of iron can be adsorbed on the alumina modified silica sol and added.

The other micronutrients are required in still smaller quantities and hence very little need be added to the sol. The quantity of iron salt that can be adsorbed on the silica sol depends on the size of particles and degree of polymerization of the particles in the sol. The smaller the particles size the more quantity of iron salt that it can adsorb. Excessive addition of iron salt can reverse the charge on the particle leading to coagulation and precipitation out from the solution in seawater conditions. In health, nutrition and medicine the compound will find use as a source of iron, other micronutrients and soluble silica. For diatom algae growth it is preferable to restrict iron salt to less than 1% of the silica contents (mole to mole) in order to get a stable sol and that which does not coagulate or precipitate in the presence of seawater. For other micronutrients like manganese less than 1.0% is sufficient but preferably 0.3% is sufficient, for zinc less than 1.0%, preferably less than 0.5% and most preferably 0.1% is sufficient and for cobalt and copper less than 0.3%, preferably 0.1% and most preferably 0.01% is sufficient. However the quantities of micronutrients can be varied depending on individual algal requirements based on detailed study.

The process of adsorption on the metalate modified silica is carried out by mixing the salt solution of the nutrient to be adsorbed and the metalate modified silica in the required proportions for a required period to ensure the proper adsorption. The completion of adsorption is generally indicated by colour changes and other known means. The order of adsorption of micro and macro nutrients is not essential for the invention. Either all the nutrients together or individually one after the other can be made adsorbed on the modified silica.

It may be noted that the above description and the examples is explanatory in its nature and should not to be construed as to limiting the scope of the invention.

Example 1

A commercial alumina modified silica sol is available called LUDOX AM from du pont. Other commercially competitive products may also be used. 100 gms. Of this product is taken in a beaker. In another beaker 10 ml of distilled water is taken and 0.3 gm of ferric chloride is dissolved. The solution of ferric chloride is added to the ludox A M with mixing. The brown color is discharged and a faint cream color results indicating the adsorption of iron on to the silica. This solution can be used as such, mixed with example 2 and used as liquid, or dried and used.

Example 2

100 gms of Ludox AM or other commercially competitive products is taken in a beaker. In another beaker 10 ml of distilled water is taken and the following is added: a) 0.1 gm of manganese chloride. b) 0.05 gm of zinc chloride c) 0.01 gm of cobalt chloride d) 0.01 gm of copper chloride. The solution of the various micronutrients is added to the Ludox AM. The micronutrient is absorbed on the ludox AM. This can be mixed with example 1 and used as such or dried and mixed with example 1 and used.

The above quantities are only indicative and it can be changed based on actual requirement.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth.

Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims.

I claim:

1. A modified silica sol for copious bloom of diatom algae, said modified silica sol comprising
   an alumina modified silica sol onto which soluble iron is adsorbed thereafter.

2. The alumina modified silica sol according to claim 1, wherein the macronutrients, micronutrients and combinations thereof are further adsorbed onto the metallate modified silica sol having adsorbed iron.

3. The alumina modified silica sol as claimed in claim 1, wherein the concentration of the iron is from 0.01% to 50% ofT weight of silica.

4. The alumina modified silica sol as claimed in claim 2, wherein the macro nutrients are selected farm a group comprising phosphorous, potassium, Nitrogen, sodium, calcium, Magnesium and sulphur or combination(s) thereof.

5. The alumina modified silica sol as claimed in claim 2, wherein the micro nutrients are selected from a group comprising Manganese, zinc, cobalt, capper, Molybdenum, nickel, Vanadium, Boron, Selenium, chromium, Iodine, Fluorine, and cadmium or combination(s) thereof.

6. The alumina modified silica sol as claimed in claim 1, wherein the sol is in either an aqueous or redispersible dried particulate form.

7. The alumina modified silica sol as claimed in claim 2, wherein the concentration of macro nutrient(s) is from 1.0% to 50% of weight of silica.

8. The alumina moaned silica sol as claimed in claim 2, wherein the concentration of micro nutrient(s) is from 0.001% to 30% of weight of silica.

9. A process for preparing the alumina modified silica sol of claim 1, said process comprising the steps of;
   (a) preparing an aqueous solution of the alumina modified silica sol;
   (b) preparing a solution of a compound selected from the group consisting of a soluble iron source, a micro nutrient and a macro nutrient;
   (b) adding the solution from step (b) to the solution from step (a); and
   (c) mixing the resultant solution; wherein
   the compound from step (b) is adsorbed onto the alumina modified silica sol.

10. The process as claimed in claim 9, wherein the concentration of the iron is from 0.01% to 50% of weight of silica.

11. The process as claimed in claim 9, wherein the macro nutrients are selected form a group comprising phosphorous, potassium, Nitrogen, sodium, calcium, Magnesium and sulphur or combination(s) thereof.

12. The process as claimed in claim 9, wherein the micro nutrients are selected from a group comprising Manganese, zinc, cobalt, copper, Molybdenum, nickel, Vanadium, Boron, Selenium, chromium, Iodine, Fluorine, and cadmium or combination(s) thereof.

13. The process as claimed in claim 9, wherein the sol is in either an aqueous or redispersible dried particulate form.

14. The process as claimed in claim 9, wherein the concentration of macro nutrient(s) is from 1.0% to 50% of weight of silica.

15. The process as claimed in claim 9, wherein the concentration of micro nutrient(s) is from 0.001% to 30% of weight of silica.

16. A process for attaining copious bloom of diatom algae, said process comprising the steps of:
   (A) adsorbing soluble iron alone or in conjunction with macro and/or micro nutrients onto a the alumina modified silica sol according to claim 1; and
   (B) adding the alumina modified silica sol to a water body; wherein said process results in the copious bloom of the diatom algae.

* * * * *